US012614709B2

(12) United States Patent (10) Patent No.: US 12,614,709 B2
Schneider et al. (45) **Date of Patent: \*Apr. 28, 2026**

(54) WORKFLOW FOR HIGH-THROUGHPUT ANALYSIS OF ANALYTES IN LIQUID SAMPLES

(71) Applicant: DH TECHNOLOGIES DEVELOPMENT PTE. LTD., Singapore (SG)

(72) Inventors: Bradley Schneider, Concord (CA); Leigh Bedford, Concord (CA); Aaron Stella, Concord (CA); Subhasish Purkayastha, Concord (CA)

(73) Assignee: DH Technologies Development Pte. Ltd., Singapore (SG)

( \* ) Notice: Subject to any disclaimer, the term of this patent is extended or adjusted under 35 U.S.C. 154(b) by 363 days.

This patent is subject to a terminal disclaimer.

(21) Appl. No.: 18/283,378

(22) PCT Filed: Mar. 21, 2022

(86) PCT No.: PCT/IB2022/052568
§ 371 (c)(1),
(2) Date: Sep. 21, 2023

(87) PCT Pub. No.: WO2022/201001
PCT Pub. Date: Sep. 29, 2022

(65) Prior Publication Data
US 2024/0177984 A1 May 30, 2024

Related U.S. Application Data

(60) Provisional application No. 63/165,854, filed on Mar. 25, 2021.

(51) Int. Cl.
*H01J 49/04* (2006.01)
*G01N 1/38* (2006.01)
(Continued)

(52) U.S. Cl.
CPC ............ *H01J 49/0454* (2013.01); *G01N 1/38* (2013.01); *G01N 27/624* (2013.01); *G01N 33/487* (2013.01)

(58) Field of Classification Search
CPC ..... H01J 49/0454; G01N 1/38; G01N 27/624; G01N 33/487
See application file for complete search history.

(56) References Cited

U.S. PATENT DOCUMENTS

| | | |
|---|---|---|
| 2012/0228490 A1 | 9/2012 | Wu et al. |
| 2015/0233866 A1 | 8/2015 | Verenchikov |
| 2025/0003929 A1* | 1/2025 | Stella ................. G01N 30/8665 |

OTHER PUBLICATIONS

International Preliminary Report on Patentability corresponding to International Patent Application No. PCT/IB2022/052568, mailed Sep. 12, 2023 (8 pages).

(Continued)

*Primary Examiner* — Nicole M Ippolito
(74) *Attorney, Agent, or Firm* — Lathrop GPM LLP; Malaika O.D. Tyson; Jason Kuchar

(57) ABSTRACT

Methods of detecting at least one analyte in at least one liquid sample are described. The method includes the steps of desalting the liquid sample, acoustically ejecting the desalted sample into an open-port interface, diluting the desalted sample, and transferring the diluted sample to an ionization source, ionizing the diluted sample, and selecting ions of interest by ion mobility.

25 Claims, 11 Drawing Sheets

(51) Int. Cl.

| | |
|---|---|
| *G01N 27/62* | (2021.01) |
| *G01N 27/624* | (2021.01) |
| *G01N 33/48* | (2006.01) |
| *G01N 33/487* | (2006.01) |

(56) References Cited

OTHER PUBLICATIONS

International Search Report and Written Opinion corresponding to International Patent Application No. PCT/IB2022/052568, mailed Jun. 7, 2022.

Miggiels Paul et al, "Novel technologies for metabolomics: More for less", Nov. 24, 2018 (Nov. 24, 2018), vol. 120, XP085898003.

Wagner Andrew et al, "Ultrahigh-Throughput and Chromatography-Free Bioanalysis of Polar Analytes with Acoustic Ejection Mass Spectrometry", Analytical Chemistry, vol. 92, No. 19, Sep. 14, 2020 (Sep. 14, 2020), p. 13525-13531, XP055827493.

Dirico Kenneth J. et al, "Ultra-High-Throughput Acoustic Droplet Ejection-Open Port Interface-Mass Spectrometry for Parallel Medicinal Chemistry", US May 1, 2020 (May 1, 2020), vol. 11, No. 6, p. 1101-1110, Retrieved from the Internet: URL: https://pubs.acs.org/doi/pdf/10.1021/acsmedchemlett.0c00066, XP055827491.

Mohammadnejad Masoumeh et al, "Rapid monitoring and sensitive determination of DDT and its metabolites in water sample using solid-phase extraction followed by ion mobility spectrometry", Dec. 5, 2016 (Dec. 5, 2016), vol. 20, No. 1, p. 23-30, XP036240080.

* cited by examiner

WORKFLOW FOR HIGH-THROUGHPUT ANALYSIS OF ANALYTES IN LIQUID SAMPLES

CROSS-REFERENCE TO RELATED APPLICATIONS

The present application is filed pursuant to 35 U.S.C. 371 as a U.S. National Phase application of International Patent Application No. PCT/IB2022/052568, which was filed Mar. 21, 2022 claiming the benefit of priority from U.S. Provisional patent application Ser. No. 63/165,854, filed Mar. 25, 2021. The aforementioned applications are incorporated by reference herein in its entirety.

BACKGROUND

Current approaches for analyzing biological fluids or liquid samples commonly employ liquid chromatography (LC)/mass spectrometry (MS) approaches. However, these methodologies typically require large sample volumes coupled with long run times to ensure adequate separations. Additionally, in workflows where data can be quickly acquired, the analysis time is still limited by column equilibration and sample loading considerations.

SUMMARY

The inventors have recognized the need for a high-throughput workflow for analyzing biological fluid or liquid samples. In particular, a rapid approach which allows for the analysis of small volumes of desalted and diluted samples.

One aspect of the disclosure relates to a method of detecting at least one analyte in at least one liquid sample, the method comprising the steps of desalting the liquid sample, acoustically ejecting the desalted sample into an open-port interface, diluting the desalted sample, and transferring the diluted sample to an ionization source, ionizing the diluted sample, and selecting ions of interest by ion mobility. In some aspects, the liquid sample is selected from the group consisting of urine, blood, oral fluid, and plasma. In one aspect, the desalted sample is diluted at a low-fold ratio. In a further aspect, the low-fold ratio is a 10-fold dilution or less. In an aspect, the desalted sample is diluted at a high-fold ratio. In a further aspect, the high-fold ratio is greater than a 10-fold dilution.

In one aspect selecting ions of interest is conducted using a differential mobility spectrometer. In another aspect, the differential mobility spectrometer includes flat or curve electrodes. In another aspect, the differential mobility spectrometer separates coeluting compounds, isobaric compounds, isomeric compounds, constitutional isomers, or diastereomers from the ions of interest. In a further aspect, the desalting step is conducted through the use of reverse phase or anion exchange phases or size-exclusion, molecular sieve, a pipette tip, and/or gel filtration.

In another aspect, the desalting step is conducted with an inline desalting device. In a further aspect, the inline desalting device is a column or a cartridge. In yet another aspect, a liquid handler houses the inline desalting device. In another aspect, the liquid handler also houses an acoustic droplet ejection transducer.

In another aspect, the method further comprises hydrolyzing the desalted sample to produce a hydrolysate and ejecting the desalted sample comprises ejecting the hydrolysate into the open port interface. In yet another aspect, after selecting the ions of interest, the method further comprises mass analyzing the ions of interest. In another aspect, the ions of interest are mass analyzed with a mass spectrometer. In a further aspect, the method comprises the step of quantifying the amount of the analyte in the liquid sample.

In some aspects, the limit of quantification is in a low ng/mL range. In other aspects, the limit of quantification is in a sub ng/mL range. In some aspects, the method further employs a multiplexing assay to analyze multiple liquid samples. In another aspect, about three samples per second or more are analyzed. In an aspect, the method is used in a high-throughput screening application or a rapid screening workflow. In yet another aspect, the analyte is at least one drug of abuse. In some aspects, the drug of abuse is selected from the group consisting of amphetamines, methamphetamines, benzodiazepines, barbiturates, marijuana, cocaine, PCP, methadone, and opioids (narcotics).

Other aspects and features of the present disclosure will become apparent to those ordinarily skilled in the art upon review of the following description of specific embodiments of the disclosure in conjunction with the accompanying figures.

BRIEF DESCRIPTION OF DRAWINGS

The objects and features of the present disclosure are set forth with particularity in the appended claims. The present invention, both as to its organization and manner of operation, together with further objects and advantages, may best be understood by reference to the following description, taken in connection with the accompanying drawings.

FIG. 1D depicts an example of analysis of the same mirtazapine sample from FIGS. 1A-1C using an open port device with acoustic injection.

DETAILED DESCRIPTION

Figure 1A:
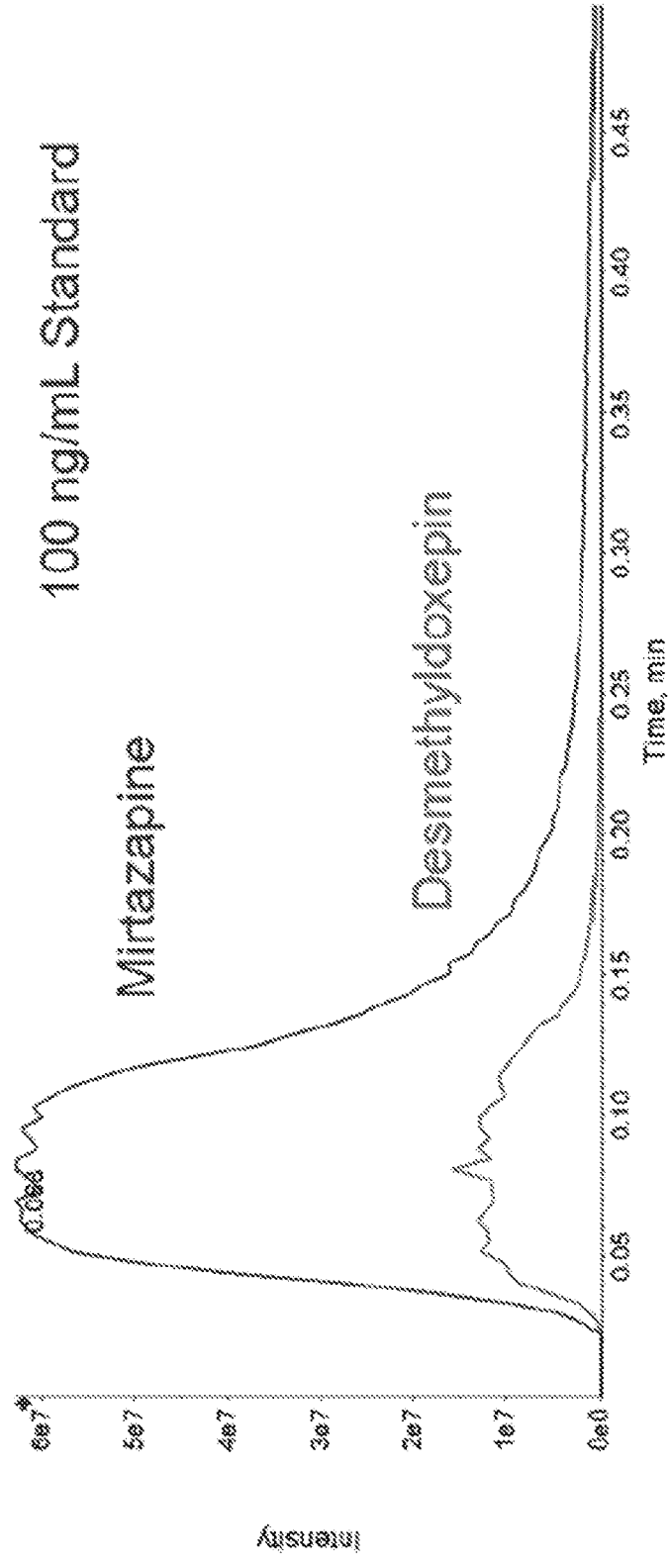
FIGS. 1A-1D illustrate flow injection analysis (FIA) data taken for 5 uL injections of a mixture of desmethyldoxepin and mirtazapine for (FIG. 1A) standards, (FIG. 1B) samples prepared in urine matrix, and (FIG. 1C) samples prepared in desalted urine matrix.

It is to be understood that this disclosure is not limited to the particular methodology, protocols, and reagents described herein and, as such, may vary. It is also to be understood that the terminology used herein is for the purpose of describing particular embodiments only and is not intended to limit the scope of the present disclosure or the appended claims.

As used herein and in the appended claims, the singular forms "a," "an," and "the" include plural reference unless the context clearly indicates otherwise.

The term "about" is used in connection with a numerical value throughout the specification and the claims denote an interval of accuracy, familiar and acceptable to a person skilled in the art. In general, such an interval of accuracy is +/−10%.

Unless defined otherwise, all technical and scientific terms used herein have the same meaning as commonly understood to one of ordinary skill in the art to which this disclosure belongs.

Analyzing biological or liquid samples often prove challenging due to the complexity of the sample matrix. Direct sample introduction processes, including, but not limited to, acoustic injection, direct flow injection, solid-phase micro-extraction, open port interface, or differential mobility spectrometry, provide several advantages, including the ability to efficiently and effectively clean-up (e.g., desalt) and concentrate samples prior to analysis. For example, an acoustic open port interface applies acoustic energy to a sample reservoir to eject very small sample volumes into a flowing stream. This allows for sample dilution that can reduce ion suppression effects. Including differential mobility spectrometry (DMS) in the analytical workflow allows for the resolution of potential isobaric interferences by selecting ions of interest based on the ion mobility differences in high- and low-field.

Embodiments of the disclosure include methods for detecting at least one analyte in a liquid sample. In an embodiment, the method includes desalting a liquid sample, acoustically ejecting the desalted sample into an open-port interface, diluting the desalted sample, and transferring the diluted sample to an ionization source, ionizing the diluted sample, and selecting ions of interest by ion mobility. The liquid sample may be a biological sample. Non-limiting examples include urine, blood, oral fluid, and plasma.

For some liquid samples, the presence of salts and other interfering substances hinders the analysis. Desalting these samples serve to reduce ion suppression effects further. In some embodiments, the desalting step is conducted using reverse-phase or anion exchange phases or size-exclusion, molecular sieve, a pipette tip, and/or gel filtration. Desalting may be conducted using pipette tips, a column, or a cartridge containing a polar substance, such as an octadecyl carbon chain (C18)-bonded silica, C8-bonded silica, pure silica, cyano-bonded silica, or phenyl-bonded silica. In an embodiment, the desalting step is conducted with an inline desalting device, such as a column or a cartridge.

In an embodiment, an inline desalting device may be housed in a liquid handler, an automated instrument that allows for the motorized transfer of reagents, samples, or other liquids. In one embodiment, the liquid handler also houses an acoustic droplet ejection transducer.

With the open port interface, the desalted sample flows continuously at a constant rate, which allows for the desalted sample to be diluted inline. In some embodiments, the desalted sample is diluted at a low-fold ratio, such as a 10-fold dilution or less. In other embodiments the desalted sample is diluted at a higher ratio such as greater than 10-fold dilution.

In an embodiment, the selection of the ions of interest is conducted using a differential mobility spectrometer. Using a differential mobility spectrometer allows for the separation of coeluting compounds, isobaric compounds, isomeric compounds, constitutional isomers, or diastereomers from the ions of interest.

In an embodiment, the method further comprises hydrolyzing the desalted sample to produce a hydrolysate and ejecting the hydrolysate into the open port interface. In some embodiments, an internal standard is added before hydrolysis, but it can be appreciated by one of ordinary skill that the internal standard may be added after hydrolysis is completed.

Hydrolysis can be chemical or enzymatic. Enzymatic hydrolysis is a process where peptide bonds in proteins are hydrolyzed using enzymes, such as proteases, peptidases, or peptide hydrolases. Proteases can be either exopeptidases, which act near the end of a polypeptide chain and include, for example, aminopeptidases and dipeptidyl peptidases, or endopeptidases, which act on nonterminal peptide bonds and include, for example, serine proteases, cysteine proteases, aspartic acid proteases, and metallo endopeptidases.

Suitable hydrolysis enzymes include, but are not limited to, β-glucuronidase, trypsin, chymotrypsin, proteases, LysC, LysN, AspN, GluC, ArgC, pronase, pepsin, and prolidase. Suitable hydrolysis enzymes also include those capable of hydrolyzing glycosidic linkages, such as those formed during metabolic processes. Non-limiting examples of these linkages include codeine-6-glucuronide and morphine-6-glucuronide linkages.

In an embodiment of the disclosure, an analyzer may be used to analyze the ions of interest. The term "analyzer" may include any suitable instrument capable of analyzing a sample, such as a biological or liquid sample. Examples of analyzers include chromatography instruments, mass spectrometers, immunoanalyzers, hematology analyzers, microbiology analyzers, and/or molecular biology analyzers.

In an embodiment, the ions of interest are mass analyzed, for example, with a mass spectrometer. The ions of interest may be introduced into the mass spectrometer with additional separation or without additional separation. Sample introduction processes that may require additional separation may include a trap and elute process module. The method may further comprise the step of quantifying the amount of the analyte in the liquid sample. When analyzing biological samples, for example, drugs of abuse, the desired limits of quantification (LOQ) are in the low ng/mL or sub ng/mL ranges. In an embodiment, the drugs of abuse include, but are not limited to, amphetamines, methamphetamines, benzodiazepines, barbiturates, LSD, ecstasy, marijuana, cocaine, PCP, methadone, stimulants, and opioids (narcotics). Urine is a common biological sample used in testing for drugs of abuse. A urinalysis or clinical urine test can detect the presence of a drug of abuse after the drug effects have worn off.

The disclosed methods allow for automization or the use of these methods in a high-throughput screening application or a rapid screening workflow. In one embodiment, the method further employs a multiplexing assay to analyze multiple liquid samples. In this embodiment about three samples per second or more are analyzed.

In an exemplary embodiment, the disclosed methods can be used as part of a routine urine toxicology screening. In this example, at least 5, at least 10, at least 15, or at least 20 analytes (i.e., drugs of abuse or drug metabolites) can be simultaneously quantitated from various (>100) urine specimens. Analytes evaluated may include, but are not limited to, 2-oxo-LSD (LSD metabolite), 6-MAM (heroine metabolite), alprazolam, a-hydroxyalprazolam, amobarbital/pentobarbital, amphetamine, benzoylecgonine (BE), buprenorphine, norbuprenorphine, butalbital, carisoprodol, clonazepam, 7-aminoclonazepam, codeine, cyclobenzaprine, N-desmethylcyclobenzaprine, desmethyldoxepin, diazepam, nordiazepam, diphenhydramine, fentanyl, norfenta-nyl, flunitrazepam, 7-aminoflunitrazepam, flurazepam, des-alkyl-flurazepam, gabapentin, hydrocodone, norhydrocodone, hydromorphone, lorazepam, ketamine, MDA, MDEA, MDMA, meperidine, normeperidine, mep-robamate, methadone, EDDP, methamphetamine, meth-ylphenidate, ritalinic acid, midazolam, mirtazapine, mor-phine, naloxone, naltrexone, oxazepam, oxycodone, noroxycodone, oxymorphone, phencyclidine (PCP), pheno-barbital, phentermine, pregabalin, pseudoephedrine, seco-barbital, tapentadol, N-desmethyltapentadol, temazepam, thc-cooh, tramadol, O-desmethyltramadol, a-hydroxytriazo-lam, zolpidem, zolpidem —COOH.

Depending on the analyte, the cutoff values for detection range between 2.5-50 ng/mL. If an analyte of interest is identified, the specimen undergoes a second confirmatory quantitative procedure using LC-MS (Liquid Chromatogra-phy-Mass Spectrometry) or LC-MS/MS (Liquid Chroma-tography-Tandem Mass Spectrometry). The disclosed meth-ods increase the specificity of downstream analysis as desalting the samples reduces matrix-related inferences and selecting the ions of interest using differential mobility spectrometry prior to mass analysis separates hard-to-re-solve ions that may co-elute. Other optimization strategies, such as increasing the processing and analysis of specimens or increasing sensitivity, may be applied to adapt the dis-closed methods to a high-throughput clinical setting.

EXAMPLES

Analysis of a Mixture of Desmethyldoxepin and Mirtazap-ine
Sample Preparation

Figure 1B:
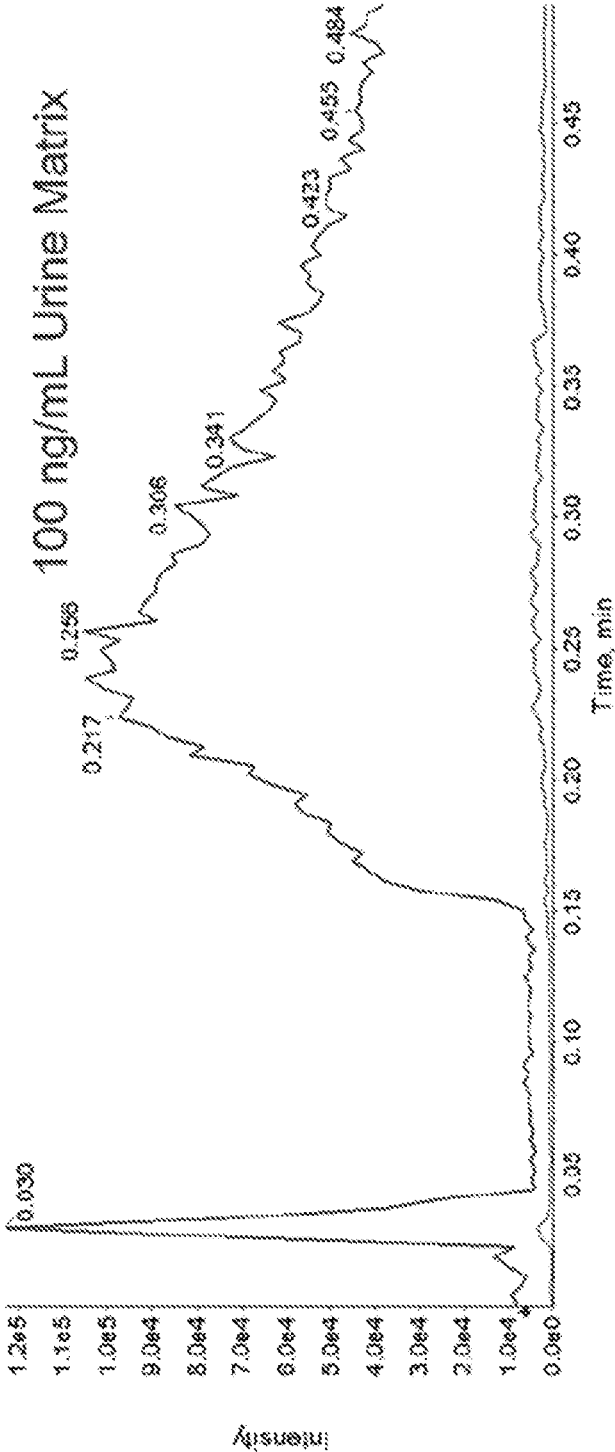
Figure 1C:
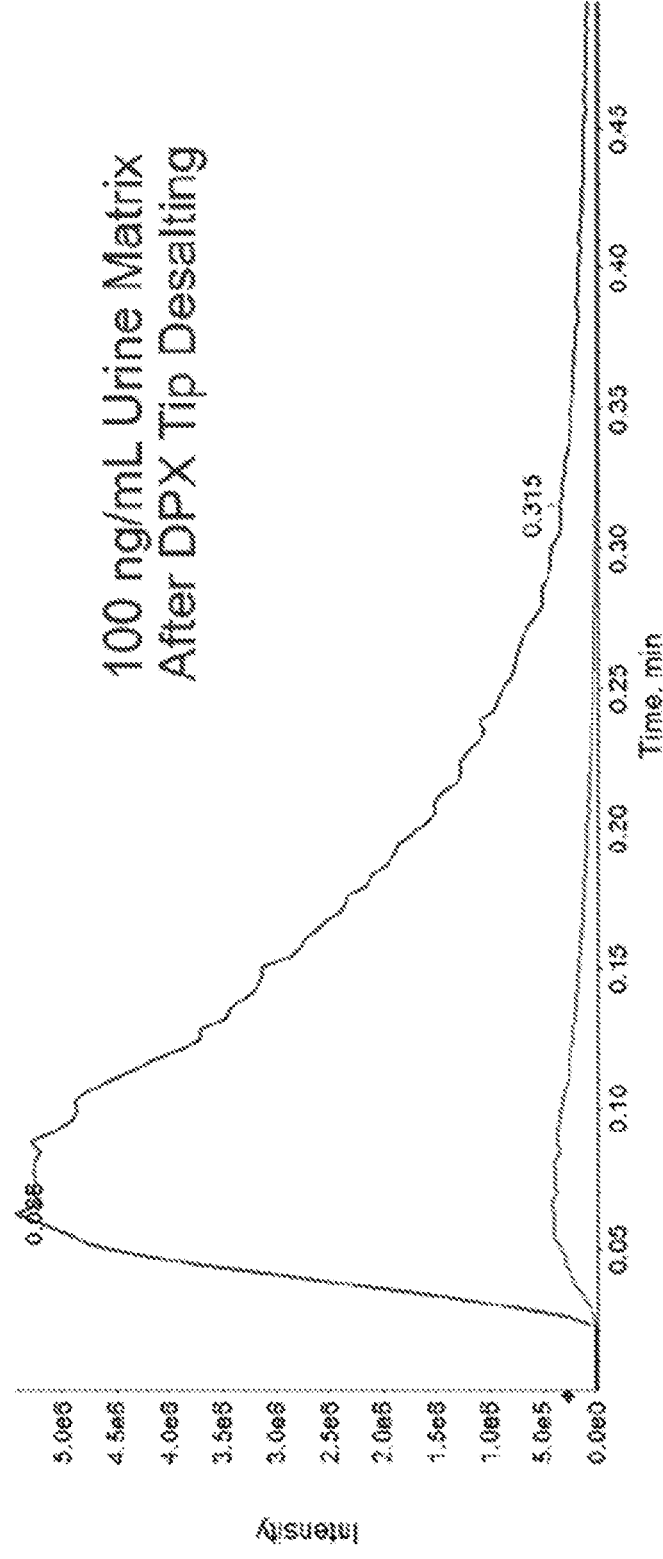

Urine samples can be collected according to the SAM-HSA guidelines (Substance Abuse and Mental Health Ser-vices Administration Center for Substance Abuse Preven-tion), available at https://www.samhsa.gov/sites/default/files/specimen-collection-handbook-2014.pdf. Urine specimens are typically submitted to certified laboratories within 24 hours after collection.
Analysis Five microliter injections of a 100 ng/mL mixture of desmethyldoxepin and mirtazapine were prepared as a stan-dard (FIG. 1A), in urine matrix (FIG. 1B), and in desalted urine matrix (FIG. 1C). The desalted mixture was desalted using an offline dispersive pipette extraction tip before flow injection analysis injection with a SelexION+ differential mobility separation device (SCIEX) on a SCIEX Triple Quad 6500+ instrument. When running the standards (FIG. 1A), typical flow injection peaks were achieved, with signal intensities on the order of 60,000,000 and 10,000,000 cps for mirtazapine and desmethyldoxepin, respectively. A typical suppression peak was observed when injecting the same concentration of drugs prepared in the urine matrix (FIG. 1B). The signal dropped out in the center of the plug, demonstrating severe suppression effects. FIG. 1C shows flow injection analysis (FIA) data after desalting the urine matrix. Samples were desalted using solid phase micro extraction (SPME) C18 fibers. The SPME fibers were con-ditioned in 200 μL of 50% methanol in water for 20 minutes. After conditioning, the SPME fibers were added to 200 μL of urine sample and were vigorously mixed for 30 minutes. The SPME fibers were then removed from the sample vials and placed into vials containing 100 μL of 100% methanol and were vigorously mixed for 5 minutes. The vials were then capped, and the contents of the vial were ready for analysis. Suppression effects were significantly reduced, resulting in a typical FIA peak shape. The signal intensity was on the order of 10-20× lower than what was observed with the standards.

Figure 1D:
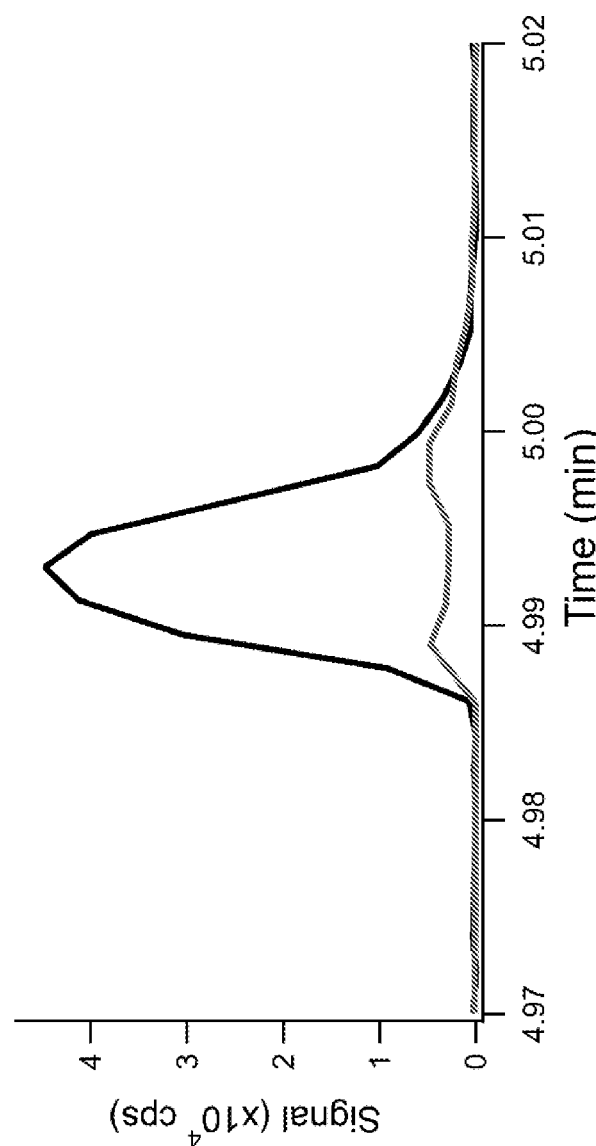

The acoustic open port interface device provides dilution of sample matrices and this can help to reduce the effects of ion suppression. However, for matrices with very high salt content such as urine, dilution alone may not be enough to completely eliminate suppression effects and/or dilution may reduce the concentration of the analyte sufficiently that it is not possible to achieve the desired LOQ. FIG. 1D shows an example of analysis of the same mirtazapine sample from FIGS. 1A-C using an open port device with acoustic injec-tion. In this case, 50 nL of sample matrix was analyzed and the sample matrix comprised urine (red trace) and desalted urine (black trace). When analyzing the urine sample using the ADE/OPP device, a peak with positive area was mea-sured, however, the peak shape showed clear signs of suppression with increased signal on the edges and a depres-sion in the center of the peak. While this represents a significant improvement over FIG. 1B, the detrimental effects of suppression are still clear. The black trace shows ADE/OPP analysis of the desalted sample with the same injection volume. In this case, a non-suppressed peak shape was generated with significantly better peak area than what was measured for the sample prepared in urine matrix.

Further dilution of the sample (by injecting smaller vol-umes) can reduce suppression to a greater extent, however, there is a trade off between decreasing suppression and decreasing analyte concentration.

Figure 2:
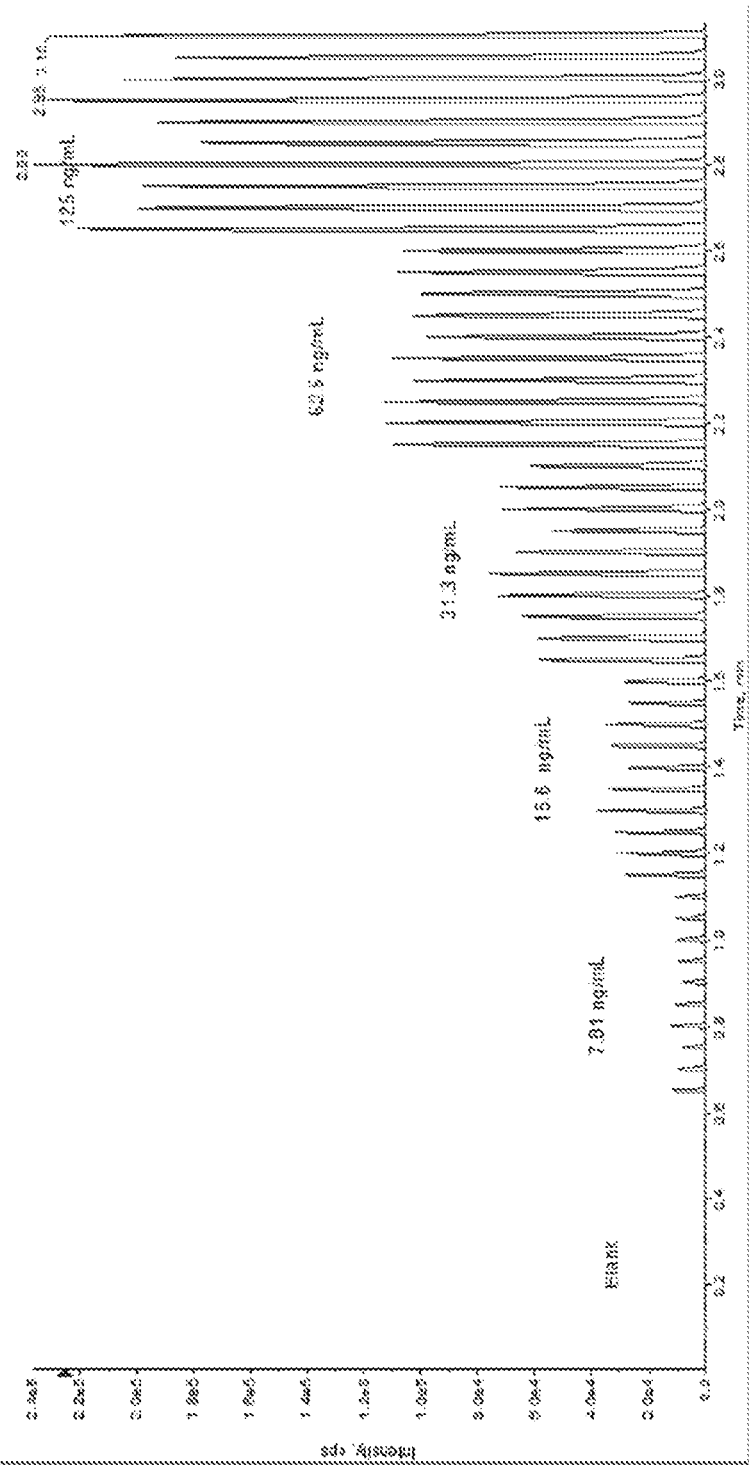
FIG. 2 illustrates calibration curve data taken for mirtazapine using 50 nL injection volumes.
Figure 3A:
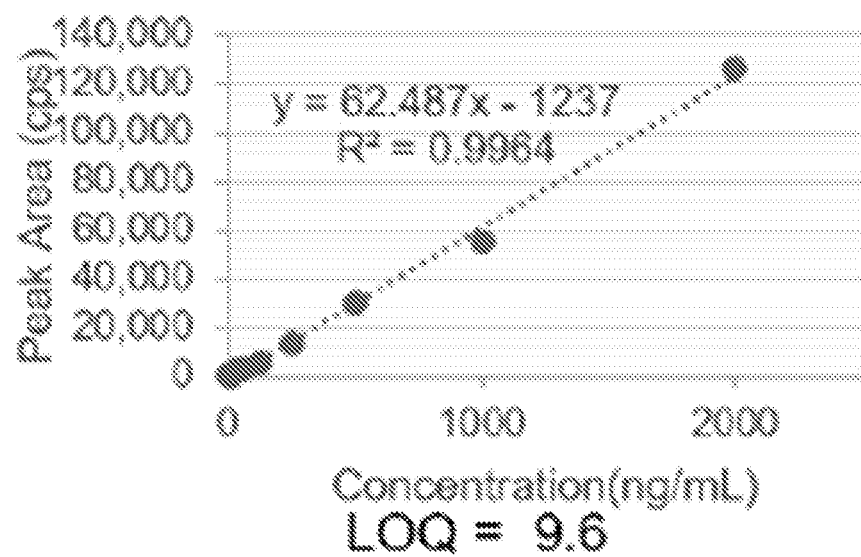
FIGS. 3A-3C illustrate the calibration curves and limit of quantitation (LOQ) for 2.5 nL (FIG. 3A), 10 nL (FIG. 3B), and 50 nL (FIG. 3C) mirtazapine samples in a desalted urine matrix.
Figure 3B:
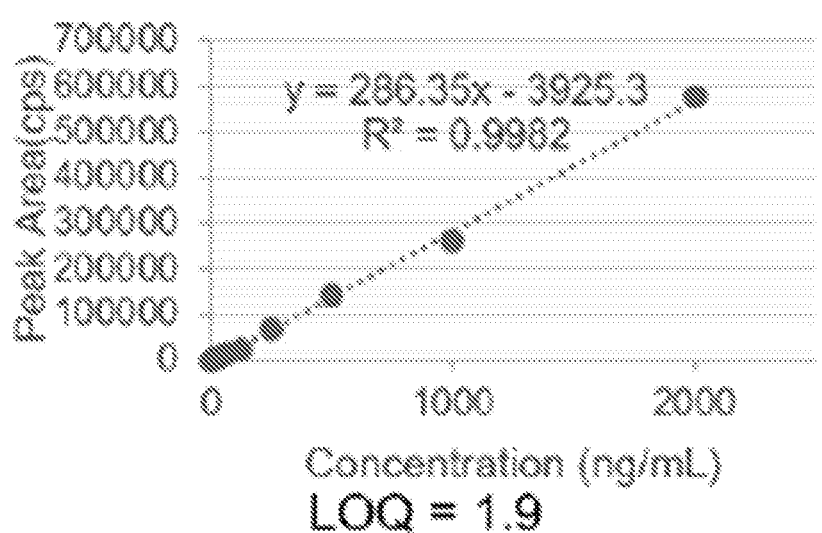
Figure 3C:
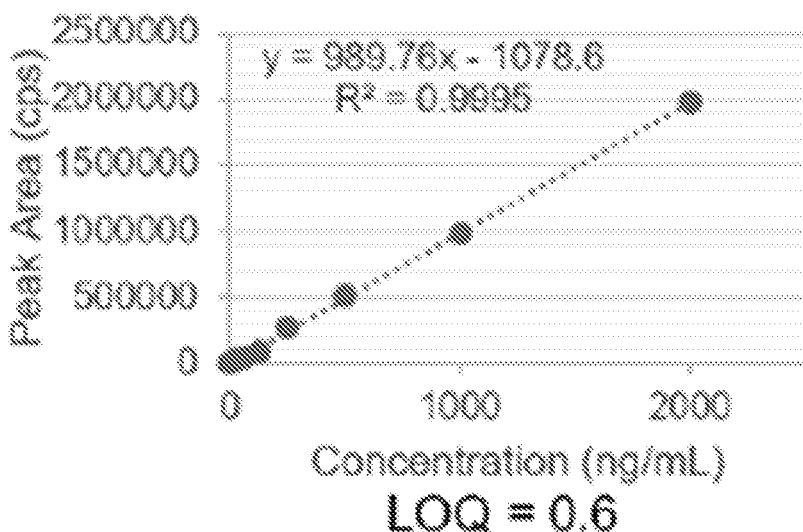
Figure 4A:
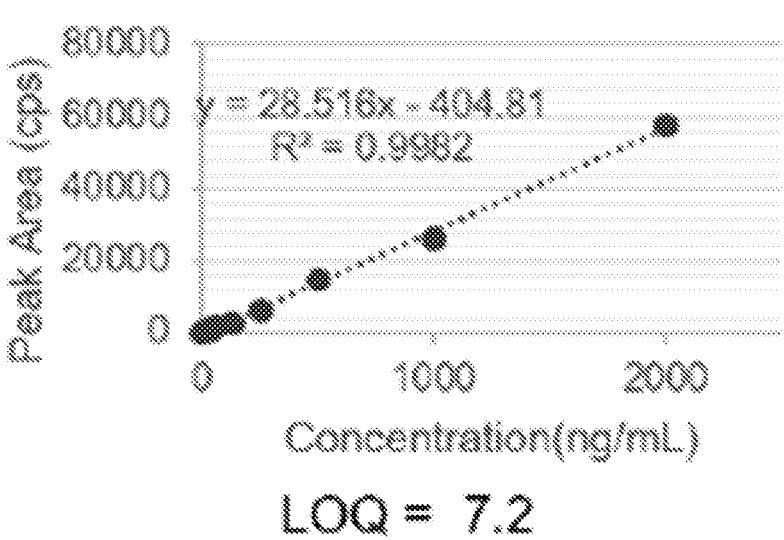
FIGS. 4A-4C illustrate the calibration curves and limit of quantitation (LOQ) for 2.5 nL (FIG. 4A), 10 nL (FIG. 4B), and 50 nL (FIG. 4C) desmethyldoxepin samples in desalted urine matrix.
Figure 4B:
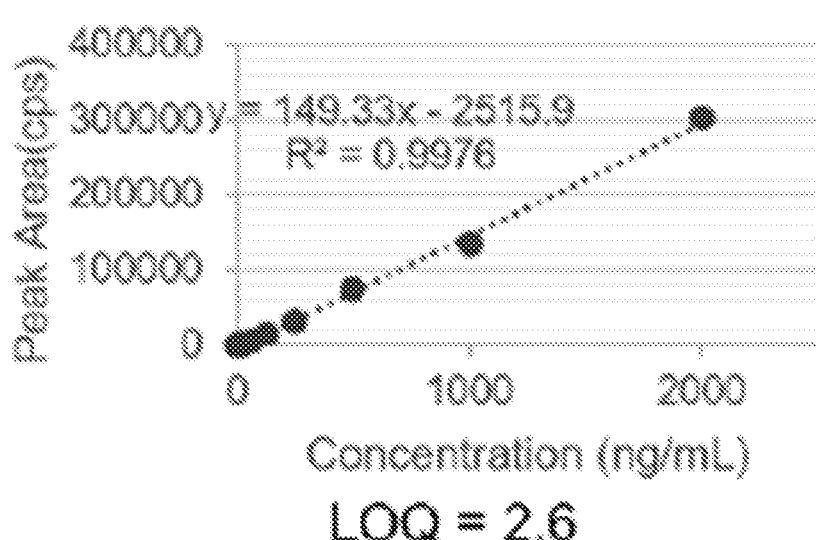
Figure 4C:
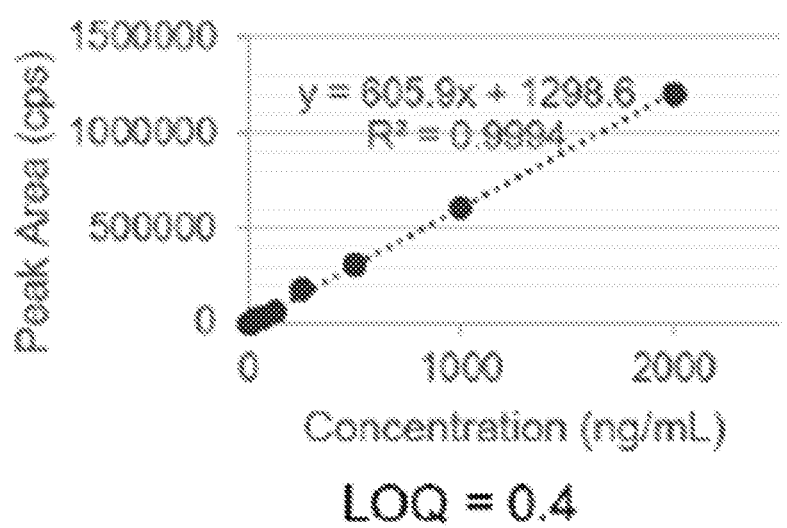
Figure 5A:
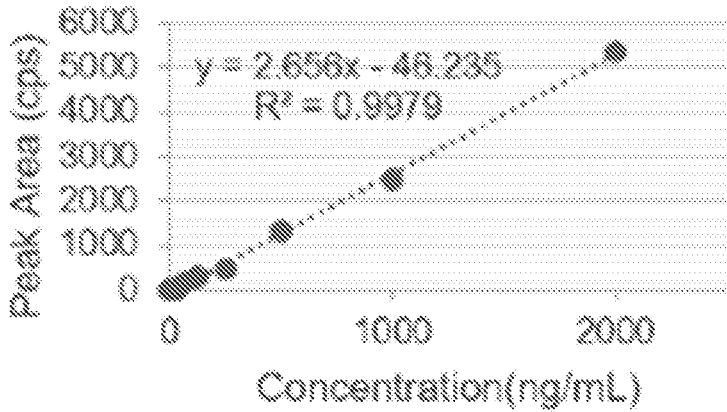
FIGS. 5A-5C illustrate mirtazapine calibration curves and LOQ for samples prepared in desalted and hydrolyzed urine; 2.5 nL (FIG. 5A), 10 nL (FIG. 5B), and 50 nL (FIG. 5C).
Figure 5B:
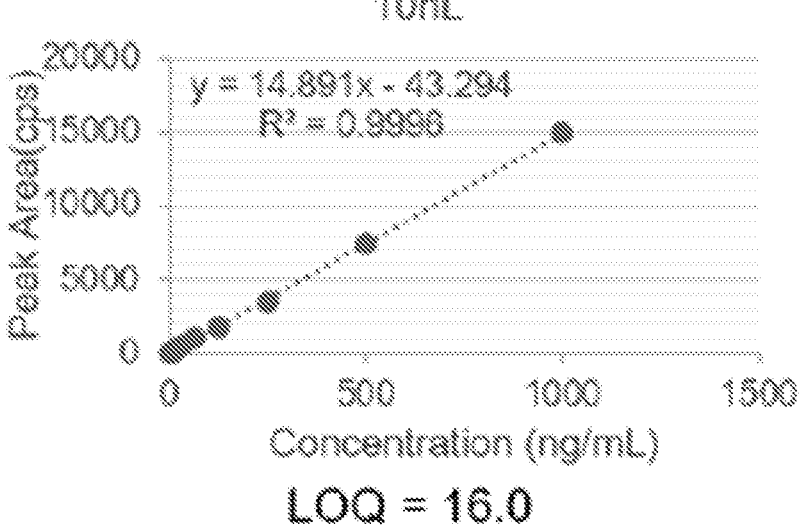
Figure 5C:
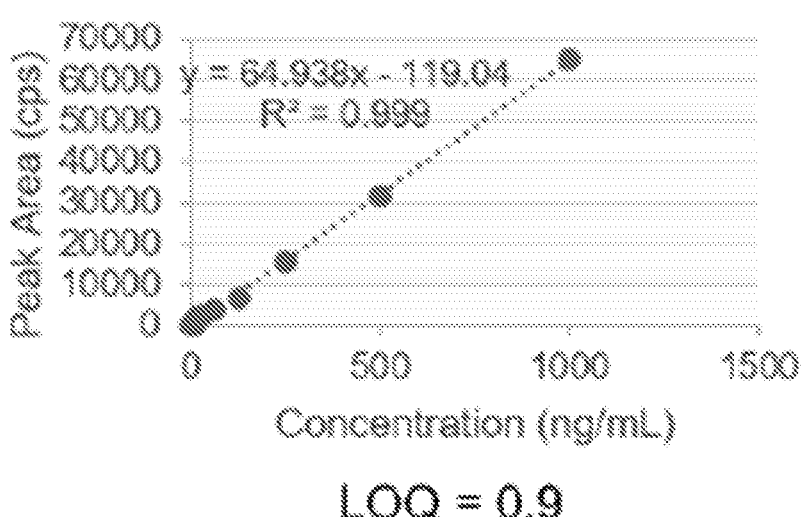
Figure 6A:
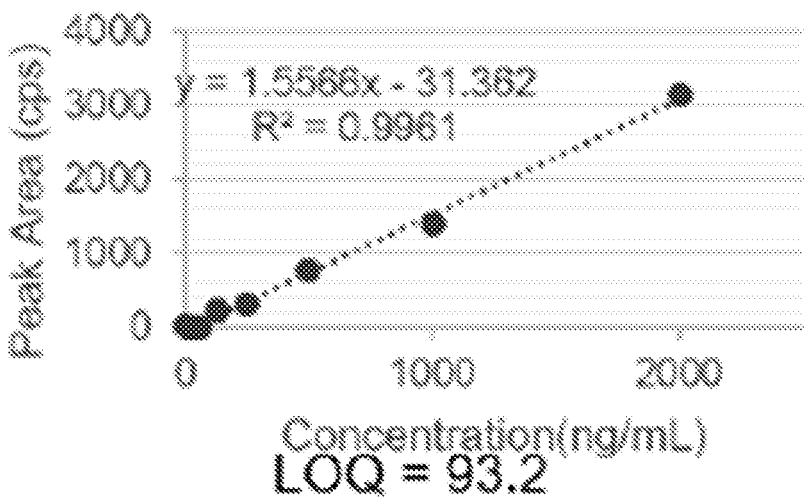
FIGS. 6A-6C illustrate desmethyldoxepin calibration curves and LOQ for samples prepared in desalted and hydrolyzed urine; 2.5 nL (FIG. 6A), 10 nL (FIG. 6B), and 50 nL (FIG. 6C).
Figure 6B:
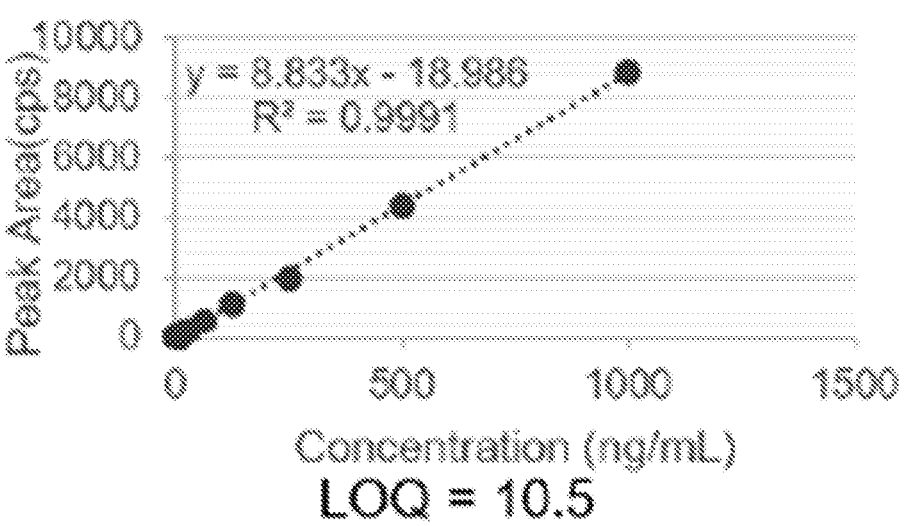
Figure 6C:
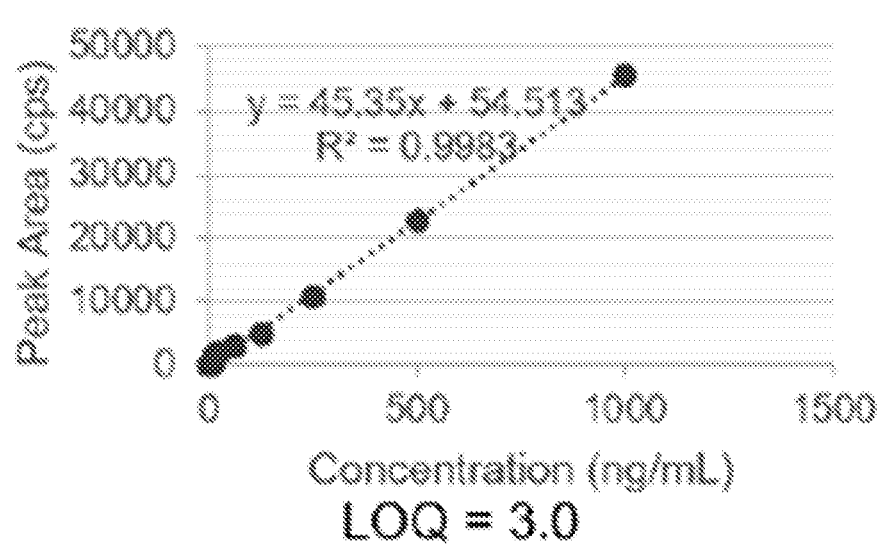

A series of sets of drug samples were prepared in urine desalted using dispersive pipette extraction pipette tips and analyzed using the acoustic open-port interface device. The dispersive pipette extraction tips were initially conditioned with 30% methanol in water. A 200 μL aliquot of urine sample was then pipetted into the conditioned tip. The urine sample was then ejected from the tip and the tip was then washed with 200 μL of water. A total of 100 μL of methanol, 0.1% formic acid was pipetted into the tip and was then ejected into a vial to elute the analyte(s) of interest. The eluate was then diluted with water containing dissolved internal standard(s). The vial was then ready for analysis. FIG. 2 shows an example of calibration curve data taken for mirtazapine using 50 nL injection volumes. FIG. 2 shows ten injections for blanks and spiked samples containing 7.81, 15.6, 31.3, 62.5, and 125 ng/mL of the drug. The lowest concentration sample (7.81 ng/mL mirtazapine) was easily differentiable from the blanks.

FIGS. 3A-3C and 4A-4C, depict calibration curves and calculated LOQs for mirtazapine and desmethyldoxepin, respectively, in desalted urine. When analyzing the desalted urine samples for both mirtazapine and desmethyldoxepin, it was possible to achieve LOQ values similar to those gen-erated previously using standards, indicating that the desalt-ing step improved the LOQ by approximately one order of magnitude as compared to samples prepared in urine. These results suggest that there may also be no need for further processing steps. A simple workflow involving offline desalting of urine samples followed by direct analysis with acoustic OPP/SelexION+/6500+ appears to be sufficient to reduce ion suppression. A series of QCs were also analyzed and shown to yield acceptable results.

An additional hydrolysis step to convert drug metabolites to the bare drug molecules may help analyze real samples (as opposed to drug spiked samples). An additional series of samples were prepared in desalted urine to ensure that the additional 10-fold dilution that occurs during hydrolysis would not be detrimental to achieving the required 20 ng/mL LOQ. Data for mirtazapine and desmethyldoxepin are shown in FIGS. 5A-5C and 6A-6C, respectively, where it is clear that the additional dilution from the hydrolysis step can be countered by injecting a larger volume of the sample For non-desalted samples, this would result in increased suppression, non-linear signal gain with injection volume, and therefore an inability to achieve the required detection limit. However, for desalted samples, the increased injection volume scales linearly with sensitivity as is evident in the slope of the calibration curves in the data for FIGS. 5A-C and 6A-C.

While the present disclosure has been described with reference to certain embodiments, it will be understood by those skilled in the art that various changes may be made and equivalents may be substituted without departing from the scope of the present disclosure or appended claims. In addition, many modifications may be made to adapt a particular situation or material to the teachings of the present disclosure without departing from its scope. Therefore, it is intended that the present disclosure not be limited to the particular embodiments disclosed, but that the present disclosure will include all aspects falling within the scope of the appended claims.

What is claimed is:

1. A method of detecting at least one analyte in at least one liquid sample, the method comprising the steps of:
    desalting the liquid sample,
    acoustically ejecting the desalted sample into an open-port interface, diluting the desalted sample, and transferring the diluted sample to an ionization source,
    ionizing the diluted sample, and
    selecting ions of interest by ion mobility.

2. The method of claim 1, wherein the liquid sample is selected from the group consisting of urine, blood, oral fluid, and plasma.

3. The method of claim 1, wherein the desalted sample is diluted at a low-fold ratio.

4. The method of claim 3, wherein the low-fold ratio is a 10-fold dilution or less.

5. The method of claim 1, wherein the desalted sample is diluted at a high-fold ratio.

6. The method of claim 5, wherein the high-fold ratio is greater than a 10-fold dilution.

7. The method of claim 1, wherein selecting ions of interest is conducted using a differential mobility spectrometer.

8. The method of claim 7 wherein the differential mobility spectrometer includes flat or curve electrodes.

9. The method of claim 7, wherein the differential mobility spectrometer separates coeluting compounds, isobaric compounds, isomeric compounds, constitutional isomers, or diastereomers from the ions of interest.

10. The method of claim 1, wherein the desalting step is conducted using reverse phase or anion exchange phases or size-exclusion, molecular sieve, a pipette tip, and/or gel filtration.

11. The method of claim 1, wherein the desalting step is conducted with an inline desalting device.

12. The method of claim 11, wherein the inline desalting device is a column or a cartridge.

13. The method of claim 11, wherein a liquid handler houses the inline desalting device.

14. The method of claim 13, wherein the liquid handler also houses an acoustic droplet ejection transducer.

15. The method of claim 1, wherein the method further comprises hydrolyzing the desalted sample to produce a hydrolysate and the step of acoustically ejecting the desalted sample comprises acoustically ejecting the hydrolysate into the open port interface.

16. The method of claim 1, wherein after selecting the ions of interest, the method further comprises mass analyzing the ions of interest.

17. The method of claim 16, wherein the ions of interest are mass analyzed with a mass spectrometer.

18. The method of claim 16, further comprising the step of quantifying the amount of the analyte in the liquid sample.

19. The method of claim 18, wherein the limit of quantification is in a low ng/ml range.

20. The method of claim 18, wherein the limit of quantification is in a sub ng/ml range.

21. The method of claim 1, wherein the method further employs a multiplexing assay to analyze multiple liquid samples.

22. The method of claim 21, wherein about three samples per second are analyzed.

23. The method of claim 16, wherein the method is used in a high-throughput screening application or a rapid screening workflow.

24. The method of claim 1, wherein the analyte is at least one drug of abuse.

25. The method of claim 24, wherein the drug of abuse is selected from the group consisting of amphetamines, methamphetamines, benzodiazepines, barbiturates, LSD, ecstasy, marijuana, cocaine, PCP, methadone, stimulants, and opioids (narcotics).

\* \* \* \* \*